United States Patent [19]

Yamada et al.

[11] Patent Number: 5,098,835
[45] Date of Patent: Mar. 24, 1992

[54] PROCESS FOR PRODUCING L-THREONINE BY FERMENTATION

[75] Inventors: Katsushige Yamada; Hiromi Tsutsui; Kyousuke Yotsumoto; Makoto Shirai, all of Aichi, Japan

[73] Assignee: Toray Industries, Inc., Japan

[21] Appl. No.: 357,690

[22] Filed: May 25, 1989

Related U.S. Application Data

[63] Continuation of Ser. No. 861,076, May 8, 1986, abandoned.

[30] Foreign Application Priority Data

May 13, 1985 [JP] Japan .................................. 60-99589
Feb. 27, 1986 [JP] Japan .................................. 61-42580

[51] Int. Cl.⁵ ...................... C12P 13/08; C12N 15/00; C12N 1/20; C12N 1/00
[52] U.S. Cl. ............................... 435/115; 435/172.1; 435/873; 435/822; 435/252.1
[58] Field of Search ...................... 435/115, 172.1, 873, 435/822, 252.1

[56] References Cited

U.S. PATENT DOCUMENTS 3,375,173 3/1968 Nishimura ............................ 435/115
3,893,888 7/1975 Tsuchida ............................ 435/115

FOREIGN PATENT DOCUMENTS 0213536 3/1987 European Pat. Off. .
8216690 12/1983 Japan .................................. 435/115
8224684 12/1983 Japan .................................. 435/115
180597 9/1985 Japan .................................. 435/115

OTHER PUBLICATIONS

Tosaka et al. (I), *Agric. Biol. Chem.* vol. 42, pp. 745–752, 1978.
Tosaka et al. (II), *Agric. Biol. Chem.* vol. 42, pp. 1501–1506, 1978.
Stanbury et al., *Principles of Fermentation Technology*, 1989, pp. 40–47.
Lynn et al., In, "Amino Acids", Addison Wesley, 1983, pp. 173–179.
Yoshinaga et al., In, "Amino Acids", pp. 405–429.
Chemical Abstracts, vol. 81, No. 4, Aug. 19, 1974, p. 310, No. 36502b.
Agric. Biol. Chem., vol. 38, No. 5, 1974, pp. 993–1000, Kase et al.

*Primary Examiner*—Douglas W. Robinson
*Assistant Examiner*—Irene Marx
*Attorney, Agent, or Firm*—Austin R. Miller

[57] ABSTRACT

Microorganisms belonging to the genus Providencia the species *rettgeri* at least leucine for the growth thereof, produce L-threonine by fermentation in higher yield and with increased amount of L-threonine accumulated.

2 Claims, No Drawings

PROCESS FOR PRODUCING L-THREONINE BY FERMENTATION

This application is a continuation of application Ser. No. 861,076, filed May 8, 1986, now abandoned.

BACKGROUND OF THE INVENTION

(a) FIELD OF THE INVENTION

This invention relates to a process for producing L-threonine by fermentation.

(b) PRIOR ART

It hitherto has been known that the microorganism belonging to the genus *Proteus* or *Providencia* of which the mutant requires L-isoleucine, can be used as microorganisms capable of producing L-threonine by fermentation (Japanese Examined Patent Publication No. 4440/1968).

However, there is room for further improvement in the capability of the strains as to the amount of L-threonine accumulated and as to the yield of L-threonine from the starting material such as glucose or fructose.

SUMMARY OF THE INVENTION

One object of the present invention is to provide an improved process for producing L-threonine by fermentation which can give a much higher accumulated amount and yield.

Another object of the invention is to provide an improved process using novel mutanized microorganisms for producing L-threonine.

These and other objects of the invention will become more apparent in the detailed description and examples hereinafter.

These objects are attained by

A process for producing L-threonine by fermentation which comprises the steps of:

(a) culturing an L-threonine producing microorganism belonging to the genus *Providencia* until L-threonine is accumulated in a culture broth, said microorganism requiring at least leucine for the growth thereof and (b) recovering the accumulated L-threonine from the culture broth.

PREFERRED EMBODIMENTS

The microorganism used in the present invention belongs to the genus *Providencia*. The genus is decided according to Bergy's Manual of Systematic Bacteriology Volume 1 (1984) pages 495 to 496. Moreover, the microorganism used in the invention requires at least L-leucine for the growth thereof and is capable of producing L-threonine. In the invention there may preferably be employed microorganisms which further have the character of lacking threonine aldolase and/or the character of having resistance to lysine analog.

In the invention "lysine analog" means (i) a substance which can inhibit the growth of the microorganism belonging to the genus *Providencia*, such an inhibition being reversed by supplement of lysine, or (ii) a substance which can repress or inhibit enzyme in the biosynthetic pathway of L-lysine.

Preferable examples of the lysine analog are S-aminoethyl-L-cystein, lysine hydroxamate, 4-hydroxylysine, and so on. As for the lysine analog S-aminoethyl-L-cystein is most preferably used.

These characters effectively operate the capability of producing L-threonine.

Moreover, there may be more preferably employed microorganisms which have further characters selected from the character requiring L-isoleucine for the growth thereof, the character having resistance to threonine analog such as $\alpha$-amino-$\beta$-hydroxyvaleric acid, and the character having resistance to methionine analog such as ethionine, adding to at least one character of the character lacking threonine aldolase and the character having a resistance to lysine analog.

These characters also effectively operate the capability of producing L-threonine. Therefore, there may be more preferably employed microorganisms which have some or all of the characters above mentioned. These characters can be given to the microorganisms by conventional methods.

In the present invention, auxotrophy, namely requiring a nutrient for the growth thereof, means a wide concept and includes the leaky type, namely the incomplete defect type, and further includes the case when auxotrophy is supplied with a biosynthetic precursor of the required nutrient.

Representative microorganisms useful for the invention are as follows:

(a) *Providencia rettgeri* NS-140

(FERM BP-1057)

This NS-140 strain has a resistance to $\alpha$-amino-$\beta$-hydroxyvaleric acid and ethionine; and requires L-isoleucine and L-leucine for the growth thereof, and was deposited with Fermentation Research Institute in Japan on Feb. 12, 1985.

(b) *Providencia rettgeri* NS1331-69

(FERM BP-1058)

This NS1331-69 strain has a resistance to $\alpha$-amino-$\beta$-hydroxyvaleric acid and ethionine; requires L-isoleucine and L-leucine for the growth thereof; and lacks threonine aldolase, and was deposited with Fermentation Research Institute in Japan on Feb. 12, 1985.

(c) *Providencia rettgeri* TP4-105-43

(FERM BP-1050)

This TP4-105-43 strain has a resistance to $\alpha$-amino-$\beta$-hydroxyvaleric acid, L-ethionine, and S-aminoethyl-L-cysteine; and requires L-isoleucine and L-leucine for the growth thereof, and was deposited with Fermentation Research Institute in Japan on July 15, 1985.

The FERM BP numbers are the access number of the Fermentation Research Institute Agency of Industrial Science and Technology, at No. 1-3, Yatabe-cho, Higashi 1-chome, Tsukuba-gun, Ibaragi-ken, 305 JAPAN, from which the microorganisms with FERM BP numbers are available to any party who requests them.

These threonine producing microorganisms can be derived as a mutant, for example, from the following parent strains of *Proteus rettgeri* which is the previous name of *Providencia rettgeri*;

(i) *Providencia rettgeri* TY-1 (FERM P-8079) This TY-1 strain has a resistance to $\alpha$-amino-$\beta$-hydroxyvaleric acid and ethionine; and requires L-isoleucine for the growth thereof and is a parent strain of NS-140.

(ii) *Providencia rettgeri* NS-133 (FERM P-8079)

This NS-133 strain has a resistance to $\alpha$-amino-$\beta$-hydroxyvaleric acid and ethionine; requires L-isoleucine for the growth thereof; and lacks threonine aldolase, and is a parent strain of NS1331-69. Moreover, NS133I-69 strain is a parent strain of TP3-105 which is a parent strain of TP4-105-43.

In the invention, methods for inducing the mutants are conventional methods such as irradiation with ultraviolet light, or treatment with N-methyl-N'-nitro-N-nitrosoguanidine or ethylmethane sulfonate, etc. After the irradiation or treatment, the mutagenized cells are spread on the minimal agar plates containing a small amount of casamino acid (Trade Mark) or yeast extract and cultivated at 30° C. for 3 or 5 days. Smaller colonies formed on the agar plates are isolated, and the colony which requires L-leucine for the growth thereof is selected.

When the microorganisms having a resistance to lysine analog is used, we define the microorganisms for the present invention as a strain which can grow and form colonies on a minimal medium supplemented with 2.5 g/l of lysine analog and of which the growth degree after the cultivation for 24 hours is at least 50%, based on the case in the absence of lysine analog. In the invention, growth degree is shown by the relative optical density of the culture broth at 660 nm when the optical density of culture broth in non-supplement of lysine analog is defined as 100%.

The processes for producing L-threonine using the microorganisms are conventional, and the microorganisms are cultivated in a conventional medium containing carbon sources, nitrogen sources, inorganic salts and other necessary organic minor nutrients.

There can be used as a carbon source, carbohydrates such as glucose, fructose, starch, cellulose hydrolysate, or molasses; organic acids such as fumaric acid, citric acid, or succinic acid; or alcohols such as glycerol.

There can be used as a nitrogen source, organic ammonium compounds such as ammonium acetate, or urea; inorganic ammonium compounds such as ammonium sulfate, ammonium chloride, ammonium phosphate, or ammonimum nitrate; ammonia gas; or aqueous ammonia.

There can be preferably used as organic nutrients corn steep liquor, polypeptone, or yeast extract.

There can be used as an inorganic salt, potassium phosphate, magnesium sulfate, ferrous sulfate 7-hydrate or 4-to 6-hydrate of manganese sulfate.

The preferable culture medium may contain 2 to 15% of carbon source, 0.5 to 4.0% of nitrogen source, and 0.001 to 0.4% of required organic material, 0 to 4% of natural organic nutrient and a minor amount of inorganic nutrient.

Cultivation is carried out under aerobic conditions such as being shaken or stirred with aeration at a temperature from 24° to 37° C. for 48 to 120 hours. During cultivation the pH of the medium is adjusted to 5 to 9.

After cultivation, L-threonine in the culture broth thus obtained can be separated by a known method, for example, by means of ion-exchange resins. In order to recover the accumulated L-threonine from the culture broth, the microorganisms are removed from the culture broth with centrifuging, and the resulting culture broth solution is adjusted to pH 2 by hydrochloric acid, and then the broth solution is passed through a strongly acidic cation exchange resin. Thereafter, the adsorbant is eluted by dilute aqueous ammonia. Ammonia is evaporated from the resulting eluent, and then the resulting solution is condensed. Alcohol is added to the resultant and left standing under cooling to give crystals of L-threonine.

The invention will be more clearly understood with reference to the following Experiments and Examples. However, these Experiments and Examples are intended to illustrate the invention and are not to be construed as limiting the scope of the invention.

EXPERIMENT 1

Isolation of the mutant strain requiring L-leucine for the growth thereof

*Providencia rettgeri* TY-1 and NS-133 were irradiated with ultraviolet light by a conventional method, respectively. The mutagenized cells were spread on the agar plates shown in Table 1.

TABLE 1

| COMPONENTS OF MEDIUM FOR AGAR PLATE | |
|---|---|
| Glucose | 0.5% |
| $(NH_4)_2SO_4$ | 0.1% |
| $KH_2PO_4$ | 0.3% |
| $K_2HPO_4$ | 0.7% |
| $MgSO_4.7H_2O$ | 0.01% |
| L-isoleucine | 0.005% |
| Polypeptone | 0.01% |
| Agar | 2% |

Then, the agar plates were incubated for 4 to 6 days at 30° C. In the colonies formed on the plate, smaller colonies were picked up from the colonies formed on the plate. NS-140 strain, which has a resistance to a $\alpha$-amino-$\beta$-hydroxyvaleric acid and ethionine and requires L-isoleucine and L-leucine, was obtained from the parent TY-1 strain. NS133I-69 strain, which has a resistance to $\alpha$-amino-$\beta$-hydroxyvaleric acid and ethionine, requires L-isoleucine and L-leucine for the growth thereof, and lacks threonine aldolase, was obtained from the parent NS-133 strain.

EXPERIMENT 2

Isolation of the mutant strain requiring L-leucine for the growth thereof and having a resistance to S-aminoethyl-L-cysteine

*Providencia rettgeri* NS133I-69 strain was irradiated with ultraviolet light by a similar manner to Experiment 1. TP3-105 strain, which has a resistance to $\alpha$-amino-$\beta$-hydroxyvaleric acid and L-ethionine, and requires L-isoleucine and L-leucine, was obtained. TP3-105 strain was treated with N-methyl-N'-nitro-N-nitrosoguanidine by a conventional method (300 $\mu$g/ml, 30° C., 10 minutes).

The mutagenized cells were spread on the agar plate shown in Table 2.

TABLE 2

| COMPONENTS OF MEDIUM FOR AGAR PLATE | |
|---|---|
| Glucose | 0.5% |
| $(NH_4)_2SO_4$ | 0.1% |
| $KH_2PO_4$ | 0.3% |
| $K_2HPO_4$ | 0.7% |
| $MgSO_4.7H_2O$ | 0.01% |
| L-leucine | 0.005% |
| S-aminoethyl-L-cysteine | 0.8% |
| L-threonine | 1.0% |
| L-isoleucine | 1.0% |
| L-methionine | 1.0% |
| Agar | 2% |

Then the agar plates were incubated for 5 to 7 days at 30° C. In the colonies formed on the plate, larger colony was picked up from colonies formed on the plate and obtained TP4-105-43 strain which has a resistance to α-amino-β-hydroxyvaleric acid, L-ethionine and S-aminoethyl-L-cysteine and requires L-isoleucine and L-leucine for the growth thereof.

EXPERIMENT 3

Test of L-leucine auxotrophy

Each strain showing in Table 4 was cultivated on nutrient agar slant for 24 hours. The resulting strains were placed on the minimal agar plate shown in Table 3 containing no L-leucine and 0.01% of L-leucine and cultivated at 30° C. for 4 days.

TABLE 3

| COMPONENTS OF MINIMAL MEDIUM FOR AGAR PLATE | |
|---|---|
| Glucose | 0.5% |
| (NH4)SO4 | 0.1% |
| KH2PO4 | 0.3% |
| K2HPO4 | 0.7% |
| MgSO4.7H2O | 0.01% |
| L-isoleucine | 0.005% |
| Agar | 2.0% |

The growth degree was measured. The mutant requiring L-leucine was determined by one which is incapable or difficult to grow in the absence of L-leucine and capable to grow in the presence of L-leucine.

The results are shown in Table 4.

*Providencia rettgeri* NS-140, NS133I-69, and TP4-105-43 apparently require L-leucine for the growth thereof, while *Providencia rettgeri* TY-1 and NS-133 which are parent strains, do not.

TABLE 4

| Microorganisms | Amount of L-leucine added (%) | Growth*) |
|---|---|---|
| *Providencia rettgeri* TY-1 (Parent strain) | 0 | + |
| *Providencia rettgeri* TY-1 (Parent strain) | 0.01 | + |
| *Providencia rettgeri* NS-140 | 0 | − |
| *Providencia rettgeri* NS-140 | 0.01 | + |
| *Providencia rettgeri* NS-133 (Parent strain) | 0 | + |
| *Providencia rettgeri* NS-133 (Parent strain) | 0.01 | + |
| *Providencia rettgeri* NS133I-69 | 0 | − |
| *Providencia rettgeri* NS133I-69 | 0.01 | + |
| *Providencia rettgeri* TP4-105-43 | 0 | − |
| *Providencia rettgeri* TP4-105-43 | 0.01 | + |

*)+: Grow
−: Not grow

EXPERIMENT 4

Test of resistance to S-aminoethyl-L-cystein

Each microorganism shown in Table 6 was cultivated in bouillon liquid at 30° C. for 16 hours with shaking, was harvested, and washed well with physiological saline. The resulting cell suspension of each microorganism was inoculated into 5 ml of the minimal medium shown in Table 5 containing 0 g/l, 2.5 g/l, 5 g/l, 7.5 g/l, 10 g/l, respectively, and cultivated at 30° C. for 14 hours.

TABLE 5

| Minimal medium | |
|---|---|
| Glucose | 0.5% |
| (NH4)SO4 | 0.1% |
| KH2PO4 | 0.3% |
| K2HPO4 | 0.7% |
| MgSO4.7H2O | 0.01% |
| L-isoleucine | 0.005% |
| L-leucine | 0.005% |
| Agar | 2.0% |

The growth degree was measured.

The results are shown in Table 6. *Providencia rettgeri* TP4-1105-43 is not inhibited the growth in the presence of the high concentration of S-aminoethyl-L-cysteine and has a strong resistance to S-aminoethyl-L-cysteine.

TABLE 6

| | Relative growth degree*) (%) Amount of S-aminoethyl-L-cysteine added (g/l) | | | | |
|---|---|---|---|---|---|
| Microorganisms | 0 | 2.5 | 5 | 7.5 | 10 |
| *Providencia rettgeri* TP3-105 | 100 (61.0) | 4 (3.6) | 4 (4.4) | 4 (4.3) | 4 (4.6)**) |
| *Providencia rettgeri* TP4-105-43 | 100 (68.2) | 92 (63.0) | 83 (56.9) | 55 (37.6) | 55 (37.5)**) |

*)Relative growth degree is shown by the relative optical density of the culture broth at 660 nm when the optical density of the cultrue broth in the absence of S-aminoethyl-L-cysteine is 100%.
**)Optical density of the culture broth at 660 nm.

EXAMPLE 1

Production of L-threonine

Each microorganism shown in Table 8 was cultivated in bouillon liquid at 30° C. for 16 hours with shaking to give a seed culture broth. Then, 4 ml of seed culture broth was inoculated into 40 ml of the fermentation medium shown in Table 7 in 1-liter shaking flask. Cultivation was carried out at 30° C. for 90 hours with shaking conditions 150 rpm, 3 cm stroke).

TABLE 7

| FERMENTATION MEDIUM*) | |
|---|---|
| Glucose (autoclaved separately) | 8% |
| (NH4)2SO4 | 2% |
| KH2PO4 | 0.1% |
| MgSO4.7H2O | 0.04% |
| Fe++ | 2 ppm |
| Mn++ | 2 ppm |
| L-Isoleucine | 0.0025% |
| L-Leucine | 0.08%**) |
| CaCO3 (autoclaved separately) | 4% |
| pH (neutralized with KOH) | 7.0 |

*)Main culture medium was previously sterilized at 115° C. for 10 minutes.
**)L-leucine was added in using NS-140 and NS-133I-69.

After cultivation, the medium was filtrated and removed off microorganisms and calcium carbonate, the amount of L-threonine accumulated in the resulting filtrate was quantitatively analyzed by automatic amino acid analyser (Produced by Japan Electric Co., JLC 200A). The results are shown in Table 8.

TABLE 8

| Microorganisms | Amount of L-threonine accumulated (g/l) | Yield of L-threonine (%)* |
| --- | --- | --- |
| *Providencia rettgeri* TY-1 (Parent strain) | 9.6 | 12.0 |
| *Providencia rettgeri* NS-140 | 13.2 | 16.5 |
| *Providencia rettgeri* NS-133 (Parent strain) | 11.5 | 14.4 |
| *Providencia rettgeri* NS133I-69 | 15.2 | 19.0 |
| *Providencia rettgeri* TP3-105 | 10.4 | 19.0 |
| *Providencia rettgeri* TP4-105-43 | 20.7 | 26.7 |

*)Yield was calculated by weight of produced L-threonine based on consumed glucose.

In examples of the present invention, the amounts of L-threonine accumulated and the yields were efficiently improved, compared with the parent strains.

EXAMPLE 2

Production of L-threonine

*Providencia rettgeri* NS-140 was cultivated in bouillon liquid medium at 30° C. for 16 hours with shaking to give a seed culture broth. 100 ml of the seed culture was transferred into a 2-liter jar fermentor, which contained 900 ml of the same fermentation medium as used in Example 1 except that 0.5% of $(NH_4)_2SO_4$ and 4.0% of glucose was used. Cultivation was carried out at 30° C. with agitation (800 rpm) and with aeration (1 liter of air per min). PH was controlled to 6.5 to 8.0 by 25% aqueous ammonia which was used as a nitrogen source. During cultivation, glucose was fed intermittently and 150 g of glucose was consumed.

After cultivation of 76 hours, 26.0 g/l for L-threonine, which was 17.3 wt % was based on glucose, was produced.

The culture broth was centrifuged and the microorganisms were removed off from the culture broth. 500 ml of the filtrate was passed through a column packed with supernatant strong cation exchange resin DIAION (Trade Mark) SK-1B [H type]. Then, the column was washed with water and thereafter the adsorbant in column was eluted by 2N aqueous ammonia. The eluent was decolorized and condensed under reduced pressure. Alcohol was added to the resultant and left standing under cooling to give crystals of L-threonine. The crystals were gathered, dried to give 11.5 g of L-threonine having 96% of the purity.

What we claim is:

1. A process for producing L-threonine by fermentation which comprises the steps of:
   (a) culturing an L-threonine producing microorganism selected from the group consisting of *Providencia rettgeri* FERM BP-1050 (TP4-105-43), *Providencia rettgeri* FERM BP-1057 (NS-140) and *Providencia rettgeri* FERM BP-1058 NS133I-69) until L-threonine is accumulated in a culture broth, and
   (b) recovering the accumulated L-threonine from the culture broth.

2. A process for producing L-threonine by fermentation which comprises the steps of:
   (a) culturing an L-threonine producing microorganism selected from the group consisting of mutants of *Providencia rettgeri* FERM BP-871 (TY-1) and *Providencia rettgeri FERM BP*-3361 (NS133) until L-threonine is accumulated in a culture broth, said microorganism requiring at least leucine for the growth thereof; and
   (b) recovering the accumulated L-threonine from the culture broth.

* * * * *